United States Patent
Yamada

(10) Patent No.: US 7,801,588 B2
(45) Date of Patent: Sep. 21, 2010

(54) X-RAY DIAGNOSTIC IMAGING SYSTEM AND X-RAY DIAGNOSTIC IMAGING METHOD

(75) Inventor: Naoki Yamada, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 20 days.

(21) Appl. No.: 11/156,587

(22) Filed: Jun. 21, 2005

(65) Prior Publication Data
US 2005/0283066 A1 Dec. 22, 2005

(30) Foreign Application Priority Data
Jun. 22, 2004 (JP) ............... 2004-184089
Jun. 9, 2005 (JP) ............... 2005-169129

(51) Int. Cl.
*A61B 6/00* (2006.01)
(52) U.S. Cl. ............... 600/431; 600/425; 378/4; 378/11; 378/901
(58) Field of Classification Search ............... 600/407, 600/410, 420, 425, 431, 458; 378/11, 98.12, 378/4, 9, 62, 98.11, 114, 131, 144, 901; 382/130
See application file for complete search history.

(56) References Cited

U.S. PATENT DOCUMENTS

| | | | | |
|---|---|---|---|---|
| 5,271,401 A * | 12/1993 | Fishman | ............... | 424/9.4 |
| 5,647,360 A * | 7/1997 | Bani-Hashemi et al. | ............... | 600/425 |
| 5,690,106 A * | 11/1997 | Bani-Hashemi et al. | ............... | 600/425 |
| 6,574,500 B2 * | 6/2003 | Keren | ............... | 600/431 |
| 6,999,555 B2 * | 2/2006 | Morf | ............... | 378/62 |
| 7,020,235 B2 * | 3/2006 | Hornegger et al. | ............... | 378/9 |
| 7,558,372 B2 * | 7/2009 | Zellerhoff | ............... | 378/98.12 |
| 2003/0036694 A1 * | 2/2003 | Liu | ............... | 600/413 |
| 2004/0066906 A1 * | 4/2004 | Hornegger et al. | ............... | 378/197 |
| 2005/0015006 A1 * | 1/2005 | Mitschke et al. | ............... | 600/431 |
| 2005/0089143 A1 * | 4/2005 | Nakano et al. | ............... | 378/98.12 |
| 2005/0165292 A1 * | 7/2005 | Simon et al. | ............... | 600/407 |
| 2005/0203373 A1 * | 9/2005 | Boese et al. | ............... | 600/407 |
| 2006/0082598 A1 * | 4/2006 | Ohishi et al. | ............... | 345/653 |
| 2006/0132483 A1 * | 6/2006 | Ohishi | ............... | 345/419 |
| 2007/0058781 A1 * | 3/2007 | Nakano et al. | ............... | 378/98.2 |
| 2009/0262897 A1 * | 10/2009 | Zellerhoff | ............... | 378/98.12 |

FOREIGN PATENT DOCUMENTS

JP    2001-149360    6/2001

* cited by examiner

*Primary Examiner*—Brian Casler
*Assistant Examiner*—Amanda Lauritzen
(74) *Attorney, Agent, or Firm*—Oblon, Spivak, McClelland, Maier & Neustadt, L.L.P.

(57) ABSTRACT

An X-ray diagnostic imaging method, comprises the steps of radiographing the predetermined area so that an image data of a first contrast image is acquired when a timing of an acquired start of the first contrast image comes, after an injection of the contrast medium into the affected part, and radiographing the predetermined area so that image data of a second contrast image is acquired when a timing of an acquired start of the second contrast image comes, after the image data of the first contrast image is acquired.

17 Claims, 5 Drawing Sheets and X-RAY DIAGNOSTIC IMAGING SYSTEM
AND X-RAY DIAGNOSTIC IMAGING
METHOD

BACKGROUND OF THE INVENTION

1. Field of the Invention

The present invention relates to X-ray diagnostic imaging systems and X-ray diagnostic imaging methods for imaging body parts inside patients using contrast medium.

2. Description of the Related Art

X-ray diagnostic imaging systems for diagnosing contrast-enhanced blood vessels by means of contrast medium each having, for example, a substantially C-shaped holder (referred to as a C-arm hereafter), an X-ray tube and an image intensifier (I. I.) at both ends of the C-arm, and an image-processing unit are well known. In general, such X-ray diagnostic imaging systems are also referred to as angiographic apparatuses or three-dimensional (3D) angiographic systems, and are capable of treatment such as to insert a catheter into the inside of the body by technicians such as doctors, and diagnosis.

Fluoroscopy is used for treatment. The fluoroscopy can provide moving images of acquired X-ray images displayed on monitors in real time, and exhibits excellent immediacy.

Meanwhile, radiography is used for diagnosis by the doctors or the like. The radiography can provide X-ray images with high spatial resolution and sharpness captured on films by high-intensity X-ray radiation.

With the X-ray diagnostic imaging systems, the doctors or the like perform angiography using a contrast medium while radiographing diagnostic areas of a patient (subject). Then, while checking the vascular running, the doctors or the like advance a guide wire or the catheter to areas to be treated so as to check the conditions of an affected part or to treat the areas.

When the guide wire or the catheter reach the affected part, the affected part is radiographed for checking the diseases of patient, and the X-ray image data is recorded in a recording unit or recording media.

Furthermore, in the X-ray diagnostic imaging systems, a method referred to as three-dimensional digital subtraction angiography (3D-DSA) is employed. In this 3D-DSA, two-dimensional (2D) image data of mask images is first acquired by performing radiography while the C-arm is rotated in a predetermined direction in a range of projection angles required to reconstruct 3D-images. Subsequently, after injection of a contrast medium into an affected part of a patient, 2D-image data of contrast images is acquired while the C-arm is rotated in a direction opposite to that for capturing the mask images. Then, subtraction between the pieces of the 2D-image data of the mask images and the contrast images whose projection angles correspond to each other is performed, and thereby 2D-image data of difference images is made. Finally, the 2D-image data of difference images is reconstructed, and displayed as 3D-image data in 3D-images.

However, in some cases of the 3D-DSA of the X-ray diagnostic imaging systems, the 3D images are required to be created from a plurality of contrast images, for example contrast images including cerebral artery and cerebral vein, and to be displayed image fused at least two pieces of the contrast images on a screen. In this case, the 2D-image data of the mask images is first acquired while the C-arm is rotated in the predetermined direction in the range of projection angles required to reconstruct the 3D images. Subsequently, after the injection of the contrast medium into the artery of the patient, the 2D-image data of the contrast images including arterial phase is acquired while the C-arm is rotated in the predetermined direction. Then, subtraction between the pieces of the 2D-image data of the mask images and the contrast images including the arterial phase whose projection angles correspond to each other is performed, and it does like that, 2D-image data of difference images including the arterial phase is made.

Next, the 2D-image data of the mask images is acquired while the C-arm is rotated in the predetermined direction. Subsequently, after the injection of the contrast medium into the vein of the patient, the 2D-image data of the contrast images including venous phase is acquired while the C-arm is rotated in the direction opposite to that for capturing the mask images. Then, subtraction between the pieces of the 2D-image data of the mask images and the contrast images including the venous phase whose projection angles correspond to each other is performed, and it does like that, 2D-image data of difference images including the venous phase is made. Subsequently, the 2D-image data of difference images including the arterial phase and the 2D-image data of difference images including the venous phase are separately reconstructed so as to create the respective pieces of the 3D-image data.

Then, the 3D-image data of the difference images including the arterial phase and the 3D-image data of the difference images including the venous phase are fused, and 3D-image data that it fused displayed as 3D-image on the screen.

That is to say, when the pieces of the 3D-image data each including the cerebral arterial phase and the cerebral venous phase are required, the contrast medium is injected into the patient twice, and the mask images are captured twice. Since the contrast medium is invasive approach for diagnosis, multiple injections of the contrast medium increase the invasiveness on the patient, and are very uncomfortable for the patient.

In addition, the multiple injections of the contrast medium into the patient and the multiple capturing of the mask images take long time, and reduce operating efficiency in diagnosis and treatment. In particular, in the 3D-DSA, difference in position of the patient during capturing the mask images and during capturing the contrast images is critical to the image quality since subtraction between the mask images and the contrast images is performed. Thus, in the 3D-DSA, prompt capturing is required.

SUMMARY OF THE INVENTION

Accordingly, the present invention has taken into consideration the above-described problems and provides an X-ray diagnostic imaging system and an X-ray diagnostic imaging method such that invasiveness on patients can be regulated, and also, 3D-DSA can be efficiently performed.

To solve the above-described problems, an X-ray diagnostic imaging method according to an aspect of the present invention comprises the steps of radiographing the predetermined area so that an image data of a first contrast image is acquired when a timing of an acquired start of the first contrast image comes, after an injection of the contrast medium into the affected part, and radiographing the predetermined area so that an image data of a second contrast image is acquired when a timing of an acquired start of the second contrast image comes, after the image data of the first contrast image is acquired.

To solve the above-described problems, an X-ray diagnostic imaging system according to an aspect of the present invention comprises a controlling unit for driving various units when a timing of an acquired start of the contrast image comes, a first image acquiring unit for acquiring a first contrast image in accordance with the commands of the controlling unit, and a second image acquiring unit for acquiring a second contrast image in accordance with the commands of the controlling unit.

In the X-ray diagnostic imaging system and the X-ray diagnostic imaging method as described above, invasiveness on patients can be regulated, and also, 3D-DSA can be efficiently performed.

DESCRIPTION OF THE PREFERRED EMBODIMENTS

An embodiment of an X-ray diagnostic imaging system and an X-ray diagnostic imaging method according to the present invention will now be described with reference to the drawings.

Figure 1:
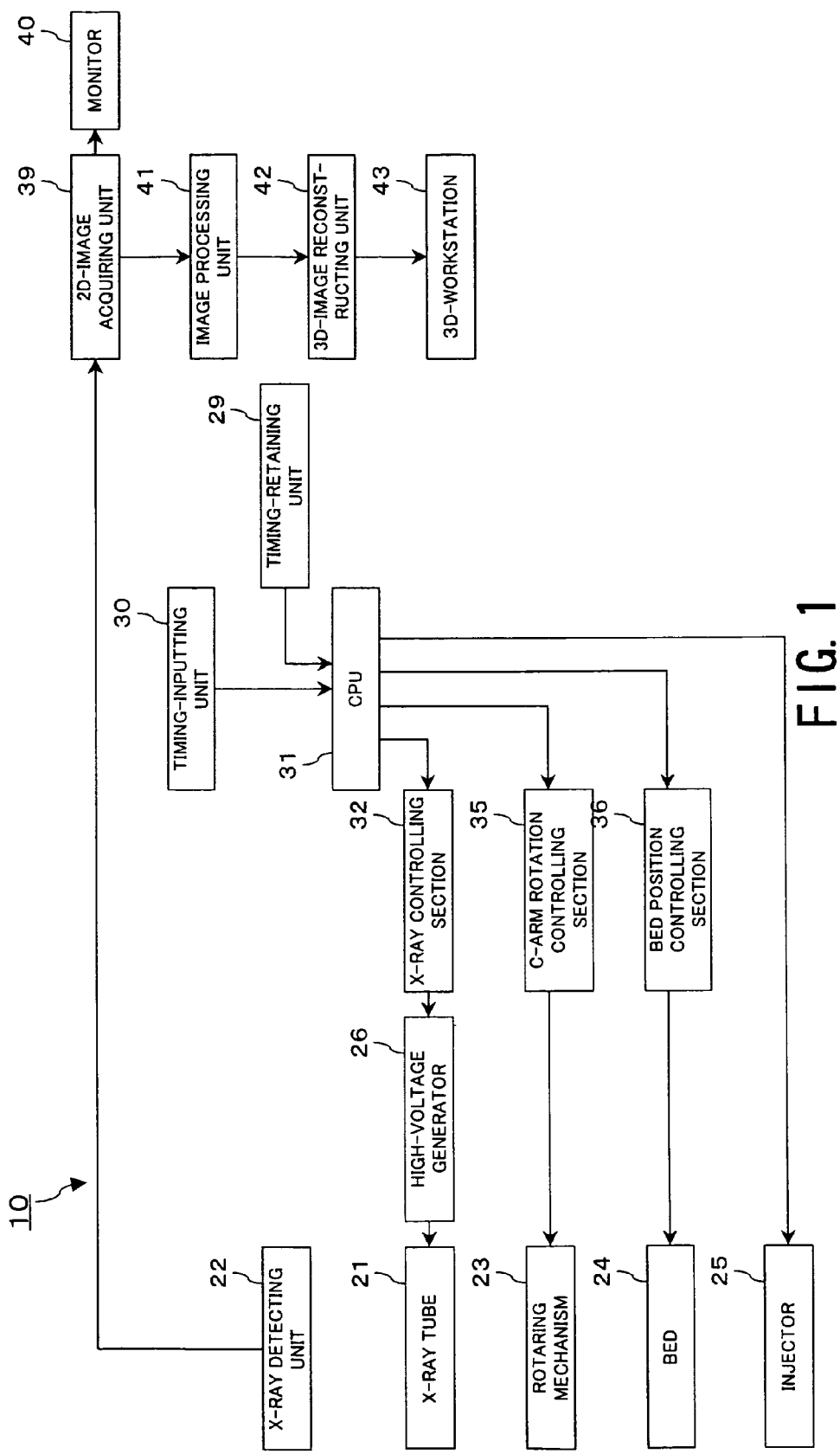
FIG. 1 is a block diagram illustrating an embodiment of an X-ray diagnostic imaging system according to the present invention.

FIG. 1 is a block diagram illustrating an embodiment of an X-ray diagnostic imaging system according to the present invention.

FIG. 1 illustrates a 3D-angiographic system as an example of the X-ray diagnostic imaging system. For example, the 3D-angiographic system has a digital angiographic (DA) mode. As for the DA mode, only X-ray image data including a contrast medium (a figure of contrast medium) is acquired by performing general radiography. The image data is then displayed and retained.

In addition, for example, the 3D-angiographic system has a digital subtraction angiography (DSA) mode. As for the DSA mode, difference image data that contains the differences between X-ray images (mask images) not including figures of the contrast medium and X-ray images (contrast images or live images) including the figures of the contrast medium is created by subtraction. The X-ray image data with clearer figures of the contrast medium or flows of the contrast medium is then displayed and retained. A case in the DSA mode will now be described.

FIG. 1 shows an X-ray diagnostic imaging system 10. The X-ray diagnostic imaging system 10 includes an X-ray tube 21 functioning as a radiation source for radiating X rays toward a patient (subject) P, and an X-ray detecting unit 22 for detecting the X-rays transmitted through the patient P held by a C-arm structure. The X-ray diagnostic imaging system 10 further includes a rotating mechanism 23 for rotating the X-ray tube 21 and the X-ray detecting unit 22 around the patient P, a bed (catheter table) 24 for laying down the patient P, and an injector 25 functioning as a contrast medium supplying unit for supplying a contrast medium to a catheter (catheter tube) inserted into an affected part of the patient P.

The X-ray tube 21 receives high-tension power from a high-voltage generator 26, and radiates the X rays depending on conditions of the high-tension power.

The X-ray detecting unit 22 includes an Image Intensifier (I. I., not shown) converting the X rays transmitted through the patient P into optical images, an optical system (not shown) for guiding the optical images output from the I. I. to a television (TV) camera (not shown) converting the optical images into TV video signals, and an analog to digital converter (not shown) for converting the TV video signals into digital signals. A video system from the I. I. to the analog to digital converter may be replaced with a flat panel detector (FPD).

Figure 2:
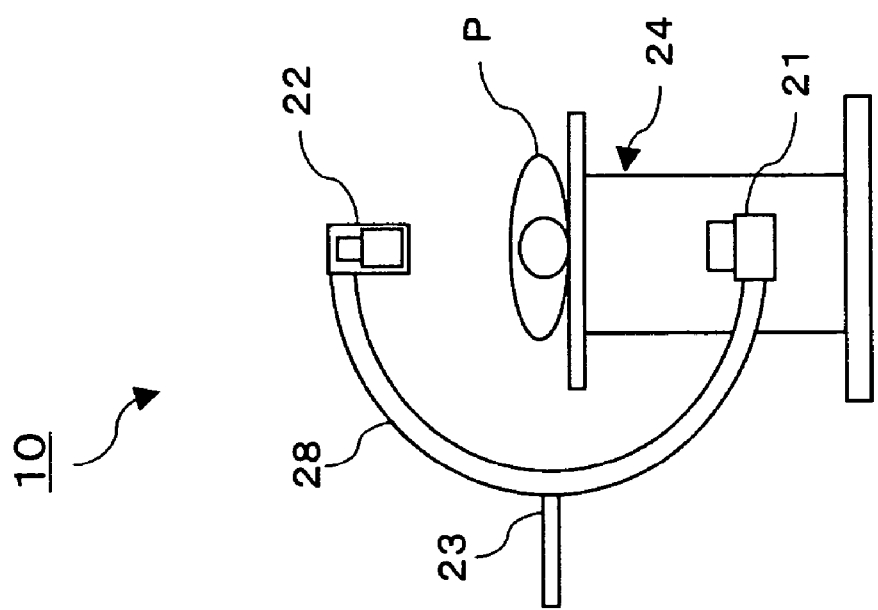
FIG. 2 is an external view of the C-arm structure included in the X-ray diagnostic imaging system.

FIG. 2 is an external view of the C-arm structure included in the X-ray diagnostic imaging system 10.

In the X-ray diagnostic imaging system 10, the X-ray tube 21 held by the C-arm structure is an under table X-ray tube type. Alternatively, the structure is an over table X-ray tube type.

As shown in FIG. 2, the X-ray tube 21 is disposed at one end of a C-arm 28, and the X-ray detecting unit 22 is disposed on the other end of the C-arm 28 such that the X-ray tube 21 and the X-ray detecting unit 22 oppose each other.

The C-arm 28 can slide such that the X-ray tube 21 moves from the lower position to the upper left position in the drawing (in an A direction), or such that the X-ray detecting unit 22 moves from the upper position to the lower left position in the drawing (in a B direction). Furthermore, the C-arm 28 can rotate around a rotational axis of the rotating mechanism 23 in a C direction.

With the C-arm structure shown in FIG. 2, doctors or the like can directly touch the patient P from the opening of the C-arm 28. Therefore, the doctors or the like can perform radiography such as angiography while performing surgery such as inserting a catheter into the patient P or performing an examination. Accordingly, the X-ray diagnostic imaging system 10 having the C-arm structure can also be used for performing interventional radiology (IVR) or the like including complicated operations of catheters.

The X-ray diagnostic imaging system 10 shown in FIG. 1 includes a timing-setting unit (not shown). The X-ray diagnostic imaging system 10 includes at least one of timing-retaining unit 29 functioning as the timing-setting unit for retaining start timings of capturing contrast images as a preset value, and timing-inputting unit 30 functioning as the timing-setting unit, with which the doctors or the like can input start timings of capturing contrast images.

In addition, the X-ray diagnostic imaging system 10 includes a central processing unit (CPU) 31 functioning as controlling unit that drives various units to capture the contrast images at the start timings of capturing the contrast images retained by the timing-retaining unit 29, an X-ray controlling section 32 for controlling X rays in accordance with commands of the CPU 31, the high-voltage generator 26 for supplying high-tension power to the X-ray tube 21 according to controls of the X-ray controlling section 32, a C-arm rotation controlling section 35 for controlling the rotating mechanism 23 in accordance with the commands of the CPU 31, and a bed position controlling section 36 for lifting the bed 24 in accordance with the commands of the CPU 31. Also, the CPU 31 can drive various units to capture the contrast images at the start timings input by the timing-inputting unit 30.

Also, the X-ray diagnostic imaging system 10 includes a 2D-image acquiring unit 39 for acquiring 2D-image data (projection data) output from the analog to digital converter of the X-ray detecting unit 22 in the form of digital signals, a monitor 40 functioning as a displaying unit for displaying 2D-images of the 2D-image data acquired by the 2D-image acquiring unit 39, an image processing unit 41 for performing subtraction so as to obtain differences between two pieces of 2D-image data whose projection angles correspond to each other, the 2D-image data being output from the 2D-image acquiring unit 39 and for creating 2D-image data with the differences, a 3D-image reconstructing unit 42 for reconstructing the 2D-image data acquired by the 2D-image acquiring unit 39 by means of information of the projection angles so as to create 3D-image data, and a 3D-workstation 43 for retaining the 3D-image data created by the 3D-image reconstructing unit 42 and for displaying the data in the form of 3D-images.

The monitor 40 displays image data made by performing the fluoroscopy before acquiring the image data of the first contrast image and the second contrast image, too.

The image processing unit 41 performs subtraction. Furthermore, the image-processing unit 41 retains the digitalized 2D-image data.

The 3D-image reconstructing unit 42 reconstructs pieces of the 2D-image data including the mask images digitalized by the image-processing unit 41 so as to create pieces of the 3D-image data. The 3D-image reconstructing unit 42 reconstructs pieces of the 2D-image data including the contrast images digitalized by the image-processing unit 41 so as to create pieces of the 3D-image data. Furthermore, the 3D-image reconstructing unit 42 reconstructs the 2D-image data including the difference images created by digitalization and subtraction by the image-processing unit 41 so as to create the 3D-image data.

The 3D-workstation 43 separately displays the 3D-image of the 3D-image data created by the 3D-image reconstructing unit 42. Alternatively, the 3D-workstation 43 displays the 3D-image of 3D-image data, fused at least two pieces of the 3D-image data created by the 3D-image reconstructing unit 42.

The 3D-image data may be supplied to the 3D-workstation 43 directly from modalities such as an X-ray computerized tomography (CT), a magnetic resonance imaging (MRI), and a single photon emission computed tomography (SPECT) that are capable of creating the 3D-image data; or indirectly via a picture archiving and communication system (PACS).

Figure 3:
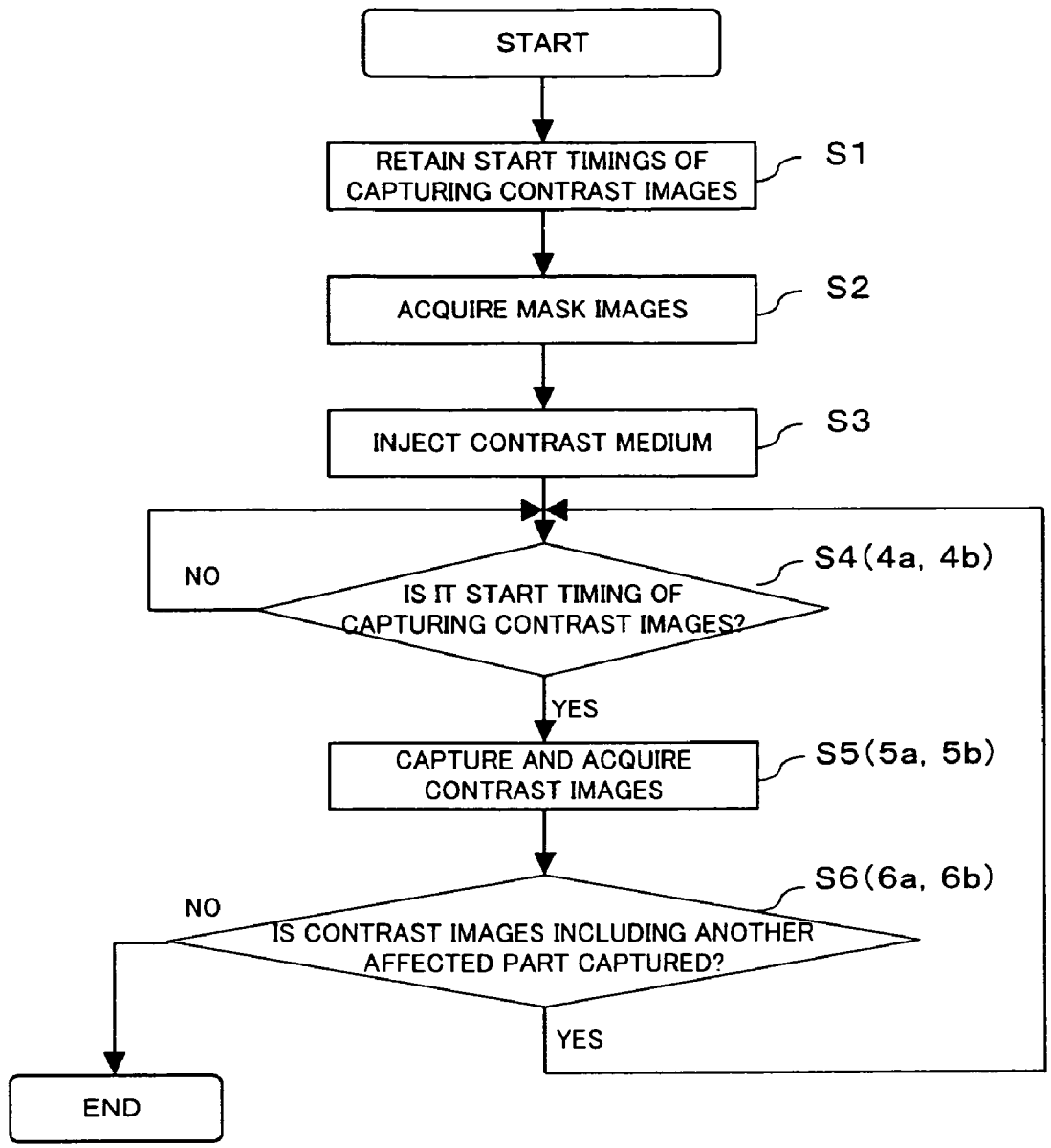
FIG. 3 is a flow chart illustrating an X-ray diagnostic imaging method according to the present invention.

Next, an X-ray diagnostic imaging method according to the present invention will now be described with reference to a flow chart shown in FIG. 3. In the following case, cerebral artery and vein are radiographed as affected parts by performing 3D-DSA. However, the affected parts are not limited to the cerebral blood vessels, or to the artery and the vein. The timing-retaining unit 29 is employed as timing-setting unit in the following case.

First, the timing-retaining unit 29 of the X-ray diagnostic imaging system 10 retains start timings of capturing contrast images including a contrast medium (a figure of contrast medium) as preset values (Step S1). For example, start timings for capturing contrast images including arterial phase and venous phase, respectively. The start timing of capturing the contrast images including the arterial phase is set according to an estimation of a time when the contrast medium reaches every part of the arteries on the basis of the start of injecting the contrast medium. On the other hand, the start timing of capturing the contrast image including the venous phase is set by estimating the time when the contrast medium coming from the artery reaches every part of the vein on the basis of the start time of injecting the contrast medium.

Then, the patient P is laid down on the bed 24 of the X-ray diagnostic imaging system 10, and radiographing conditions are set by the doctors or the like. According to the conditions, the CPU 31 controls the X-ray controlling section 32, the C-arm rotation controlling section 35 and the bed position controlling section 36 to set the output of the X-ray tube 21, the position of the C-arm 28 by means of the rotating mechanism 23, and the position of the bed 24, respectively, so as to perform the 3D-DSA. In the 3D-DSA, a radiography system is rotated around the body axis of the patient P while the contrast images including the affected part are acquired as the contrast medium injected into the patient P is traced.

Figure 4:
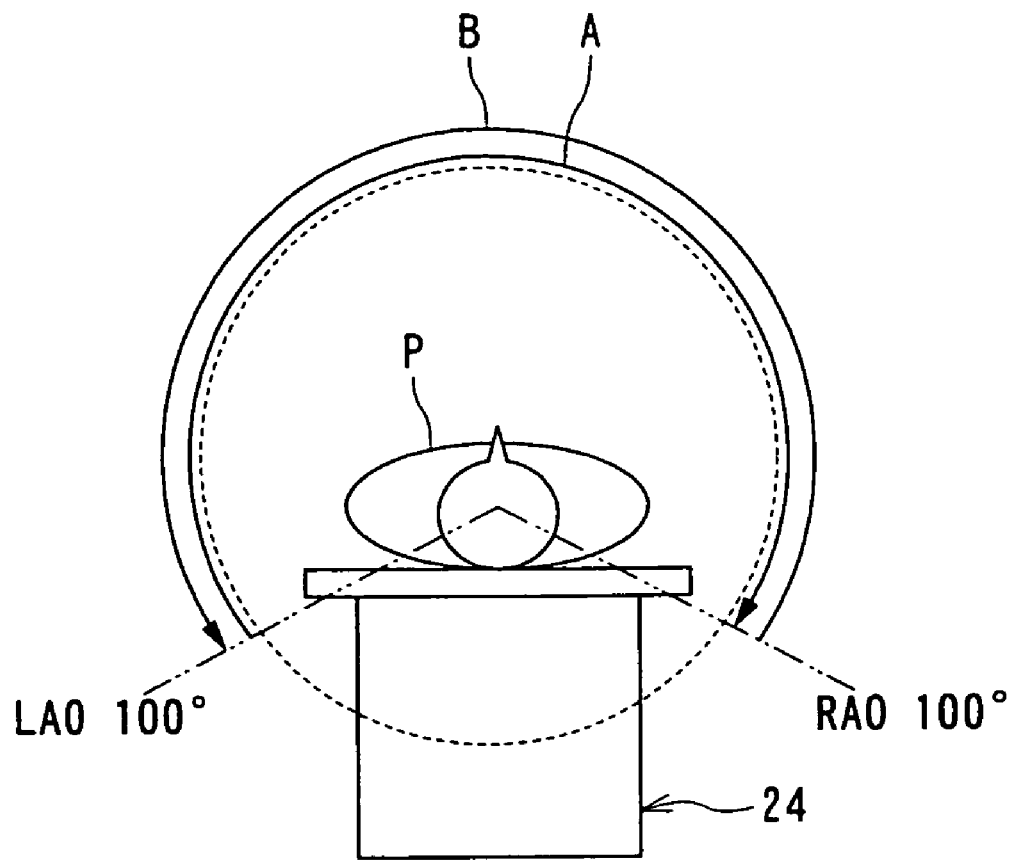
FIG. 4 is a schematic view illustrating the 3D-DSA.

FIG. 4 is a schematic view illustrating the 3D-DSA.

FIG. 4 is a schematic view of the structural components of the X-ray diagnostic imaging system 10 shown from a position adjacent to the head of the patient P. In a general 3D-DSA, mask images are captured in an A direction, first contrast images are captured in a B direction, second contrast images are captured in the A direction, and the subsequent contrast images are captured in the alternate directions.

In the 3D-DSA, the doctors or the like first inserts a catheter into the cervix of the patient P while observing fluoroscopic images displayed on the monitor 40. The mask images are acquired by the 2D-image acquiring unit 39 of the X-ray diagnostic imaging system 10 shown in FIG. 1 in the form of the 2D-image data (Step S2). That is to say, the 2D-image data is acquired while the C-arm 28 is rotated around a predetermined area, for example the head of the patient P, in a predetermined direction by predetermined angles, for example in the A direction shown in FIG. 4 by 200° (from LAO (Left Arterior Oblique view) 100° to RAO (Right Arterior Oblique view) 100°).

In the acquisition of the 2D-image data in Step S2, the rotating mechanism 23 is controlled in accordance with the commands of the CPU 31; and the radiography is repeated while the C-arm 28 is rotated around the head of the patient P in the A direction by 200° (while changing the projection angles) at predetermined angular intervals, for example 1°, such that X-ray intensity distributions for 200° (two hundred patterns of X-ray intensity distributions) are acquired. The data of the two hundred patterns of the X-ray intensity distributions is displayed on the monitor 40 in the form of the 2D images, and at the same time, retained by the image-processing unit 41.

Next, according to the commands of the CPU 31, the contrast medium is injected into the cervix from the catheter via the injector 25 (Step S3).

The CPU 31 determines whether a predetermined time period passed after the injection of the contrast medium into the cervix and whether it is the start timing of capturing the contrast images retained by the timing-retaining unit 29 in Step S3 (Step S4). For example, the CPU 31 determines whether it is the start timing of capturing the contrast images including the arterial phase (Step S4a).

If it is "YES" in Step S4, i.e. when it is the start timing of capturing the contrast images, the contrast images are captured and acquired by the 2D-image acquiring unit 39 in the form of the 2D-image data (Step S5). For example, the contrast images including the arterial phase are captured and acquired by the 2D-image acquiring unit 39 (Step S5a). That is to say, the 2D-image data including the arterial phase is acquired while the rotating mechanism 23 is controlled in accordance with the commands of the CPU 31 such that the C-arm 28 is rotated around the head of the patient P in a predetermined direction by predetermined angles, for example in the B direction shown in FIG. 4 by 200° (from RAO 100° to LAO 100°).

In the acquisition of the 2D-image data in Step S5, the radiography is repeated while the C-arm 28 is rotated in the B direction by 200° at predetermined angular intervals, for example 1°, such that X-ray intensity distributions for 200° are acquired. The data of the two hundred patterns of the X-ray intensity distributions is displayed on the monitor 40 in the form of the 2D images, and at the same time, retained by the image-processing unit 41.

Next, it is determined whether contrast images including another affected part other than that captured in Step S5 are captured (Step S6). For example, followed by the capture of the contrast images including the arterial phase, it is determined whether the contrast images including the venous phase are captured (Step S6a).

If it is "YES" in Step S6, i.e. when the contrast images including another affected part are to be captured, the process returns to Step S4. For example, if it is "YES" in Step S6a, i.e. when the contrast images including the venous phase are to be captured after the capture of the contrast images including the arterial phase, the CPU 31 determines whether it is the start timing of capturing the contrast images including the venous layer phase (Step S4b).

If it is "YES" in Step S4b, i.e. when it is the start timing of capturing the contrast images including the venous phase, the contrast images including the venous phase are captured and acquired by the 2D-image acquiring unit 39 in the form of the 2D-image data (Step S5b). That is to say, the 2D-image data including the venous phase is acquired while the rotating mechanism 23 is controlled in accordance with the commands of the CPU 31 such that the C-arm 28 is rotated around the head of the patient P in a predetermined direction by predetermined angles, for example in the A direction shown in FIG. 4 by 200° (from LAO 100° to RAO 100°).

On the other hand, if it is "NO" in Step S4, i.e. when it is not the start timing of capturing the contrast images, the system waits to capture the contrast images until the start timing.

As described above, according to the flow chart shown in FIG. 3, the first contrast images including the arterial phase are captured in Step S5a. Subsequently, the process returns from Step S6a to Step S4b, and the second contrast images including the venous phase are captured in Step S5b.

On the other hand, if it is "NO" in Step S6, i.e. when the contrast images including another affected part are not to be captured, the capture of the contrast images is finished.

The image-processing unit 41 performs subtraction so as to obtain differences between the pieces of the 2D-image data of the mask images and the contrast images whose projection angles correspond to each other. For example, subtraction between the 2D-image data of the mask images acquired in Step S2 and the 2D-image data of the contrast images including the arterial phase acquired in Step S5a is performed for each projection angles.

Also, subtraction between the 2D-image data of the mask images acquired in Step S2 and the 2D-image data of the contrast images including the venous layer acquired in Step S5b is performed for each projection angles. The 2D-image data after subtraction is sent to the 3D-image reconstructing unit 42.

The 3D-image reconstructing unit 42 reconstructs discretized areas. As an example of reconstructing methods, filtered back projection (reverse projection of a filter) proposed by Feldkamp et al. will now be described. First, the two hundred frames of the acquired DSA images are convoluted by an appropriate convolution filter (correction filter) such as Sheep-and-Logan and Ramachandran.

Next, the 3D-image reconstructing unit 42 performs backprojection operation on the convoluted results so as to project the image data back. Thus, the reconstructed image data, i.e. 3D-image data, is acquired. The 3D-image data created by the above-described reconstruction is retained in a memory (not shown), and the 3D-image reconstruction is completed.

Specifically, in the 3D-image reconstructing unit 42, the pieces of the 2D-image data of the mask images, the contrast images including the arterial phase, and the contrast images including the venous phase retained in the image-processing unit 41 are separately reconstructed such that the respective pieces of the 3D-image data are created. Also, in the 3D-image reconstructing unit 42, the piece of the 2D-image data of the difference images between the mask images and the contrast images including the arterial phase, and the piece of the 2D-image data of the difference images between the mask images and the contrast images including the venous phase created by the image-processing unit 41 are separately reconstructed such that the respective pieces of the 3D-image data are created.

When the X-ray detecting unit 22 shown in FIG. 1 includes an I. I., the 3D-image reconstructing unit 42 may correct the distortion of the I. I., and then convolute the DSA images by means of a correction filter according to the filtered back projection.

The 3D-image data created by the 3D-image reconstructing unit 42 is sent to the 3D-workstation 43, and displayed on a screen (not shown) of the 3D-workstation 43 in the form of 3D images.

Specifically, the 3D-workstation 43 retains and selectively displays the 3D-image data created by reconstructing the 2D-image data of the mask images, the contrast images including the arterial phase, and the contrast images including the venous phase; and the 3D-image data created by reconstructing the 2D-image data of the difference images. The 3D-workstation 43 separately displays the pieces of the 3D-image data created by the 3D-image reconstructing unit 42. Alternatively, the 3D-workstation 43 displays the 3D-image data fused at least two pieces of the 3D-image data created by the 3D-image reconstructing unit 42.

In this X-ray diagnostic imaging system 10, the pieces of the 2D-image data of the mask images and the contrast images are acquired. However, the piece of the 2D-image data of the mask images is not necessarily acquired. When only the pieces of the 2D-image data of the contrast images are acquired, the 3D-image reconstructing unit 42 reconstructs the pieces of the 2D-image data of the contrast images including the arterial phase and the contrast images including the venous phase retained by the image-processing unit 41 so as to create the respective pieces of the 3D-image data. The 3D-workstation 43 retains and displays the 3D-image data created by the 3D-image reconstructing unit 42.

According to the X-ray diagnostic imaging system 10 and the X-ray diagnostic imaging method of the present invention, the contrast images including the arterial phase and the venous phase can be captured at one time. Thus, invasiveness on patients can be regulated, and also, 3D-DSA can be efficiently performed.

Figure 5:
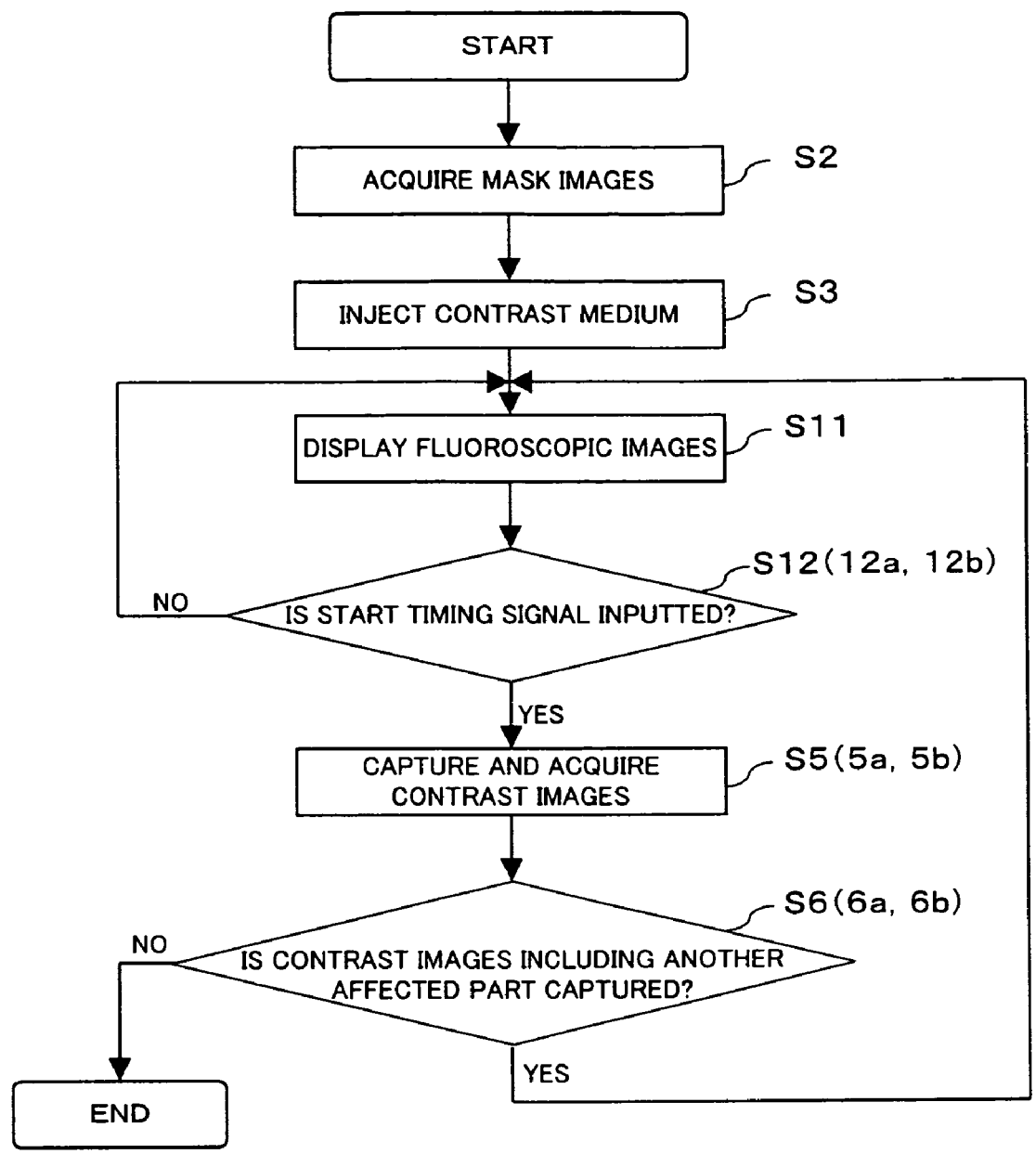
FIG. 5 is a flow chart illustrating a modification example of the X-ray diagnostic imaging method according to the present invention.

FIG. 5 is a flow chart illustrating a modification example of the X-ray diagnostic imaging system according to the present invention. The timing-inputting unit 30 of the X-ray diagnostic imaging system 10 shown in FIG. 1 is employed as timing-setting unit in the following case. In the following case, cerebral artery and vein are radiographed as affected parts by performing 3D-DSA. However, the affected parts are not limited to the cerebral blood vessels, or to the artery and the vein.

The timings when the contrast medium comes into the affected part, for example, the artery and the vein, after the injection of the contrast medium vary depending on the affected parts or the speed of the injection of the contrast medium. Accordingly, in this modification of the X-ray diagnostic imaging system according to the present invention, the start timings of capturing the contrast images are manually input.

First, the patient P is laid down on the bed 24 of the X-ray diagnostic imaging system 10, and radiographing conditions are set by the doctors or the like. According to the conditions, the CPU 31 controls the X-ray controlling section 32, the C-arm rotation controlling section 35, and the bed position controlling section 36 to set the output of the X-ray tube 21, the position of the C-arm 28 by means of the rotating mechanism 23, and the position of the bed 24, respectively, so as to perform the 3D-DSA.

In the 3D-DSA, the doctors or the like first inserts a catheter into the cervix of the patient P while observing fluoroscopic images displayed on the monitor 40. The mask images are acquired by the 2D-image acquiring unit 39 of the X-ray diagnostic imaging system 10 shown in FIG. 1 in the form of the 2D-image data (Step S2). That is to say, the 2D-image data is acquired while the C-arm 28 is rotated around a predetermined area, for example the head of the patient P, in a predetermined direction by predetermined angles, for example in the A direction shown in FIG. 4 by 200° (from LAO 100° to RAO 100°). The acquired 2D-image data is displayed on the monitor 40 in the form of the 2D images, and at the same time, retained by the image-processing unit 41.

Next, according to the commands of the CPU 31, the contrast medium is injected into the cervix from the catheter via the injector 25 (Step S3).

The doctors or the like determine whether the contrast medium comes into the affected part while observing the fluoroscopic images displayed on the monitor 40 (Step S11). When the doctors or the like determine that the contrast medium comes into the affected part, the doctors or the like manually input the start timing of capturing the contrast images by the timing-inputting unit 30 so as to input a start timing signal for capturing the contrast images to the CPU 31. For example, when the doctors or the like determine that the contrast medium comes into the artery of the affected parts, they manually input the start timing of capturing the contrast images including the arterial phase by the timing-inputting unit 30 so as to input the start timing signal for capturing the contrast images including the arterial phase to the CPU 31.

The CPU 31 determines whether the start timing signal for capturing the contrast images is inputted by the timing-inputting unit 30 (Step S12). For example, the CPU 31 determines whether the start timing signal for capturing the contrast images including the arterial phase is inputted by the timing-inputting unit 30 (Step S12a).

If it is "YES" in Step S12, i.e. when the start timing signal for capturing the contrast images is inputted by the timing-inputting unit 30, it considered the start timing of capturing the contrast images, and the fluoroscope is stopped. Next, the contrast images are captured and acquired by the 2D-image acquiring unit 39 in the form of the 2D-image data (Step S5). For example, the contrast images including the arterial phase are captured and acquired by the 2D-image acquiring unit 39 (Step S5a). That is to say, the 2D-image data including the arterial phase is acquired while the rotating mechanism 23 is controlled in accordance with the commands of the CPU 31 such that the C-arm 28 is rotated around the head of the patient P in a predetermined direction by predetermined angles, for example in the B direction by 200° (from RAO 100° to LAO 100°). The acquired 2D-image data is displayed on the monitor 40 in the form of the 2D images, and at the same time, retained by the image-processing unit 41.

Next, it is determined whether contrast images including another affected part other than that captured in Step S5 are captured (Step S6). For example, followed by the capture of the contrast images including the arterial phase, it is determined whether the contrast images including the venous phase are captured (Step S6a).

If it is "YES" in Step S6, i.e. when the contrast images including another affected part are to be captured, the process returns to Step S11. For example, if it is "YES" in Step S6a, i.e. when the contrast images including the venous phase are to be captured after the capture of the contrast images including the arterial phase, the doctors or the like determine whether the contrast medium comes from the artery into the vein while observing the fluoroscopic images displayed on the monitor 40 (Step S11). When the doctors or the like determine that the contrast medium comes into the vein, the doctors or the like manually input the start timing of capturing the contrast images including the venous phase by the timing-inputting unit 30 so as to input a start timing signal for capturing the contrast images including the venous phase to the CPU 31.

The CPU 31 determines whether the start timing signal for capturing the contrast images including the venous phase is inputted by the timing-inputting unit 30 (Step S12b).

If it is "YES" in Step S12b, i.e. when the start timing signal for capturing the contrast images including the venous phase is inputted by the timing-inputting unit 30, it considered the start timing of capturing the contrast images, and the fluoroscope is stopped. Next, the contrast images including the venous phase are captured and acquired by the 2D-image acquiring unit 39 in the form of the 2D-image data (Step S5b). That is to say, the 2D-image data including the venous phase is acquired while the rotating mechanism 23 is controlled in accordance with the commands of the CPU 31 such that the C-arm 28 is rotated around the head of the patient P in a predetermined direction by predetermined angles, for example in the A direction by 200° (from LAO 100° to RAO 100°).

If it is "No" in Step S12, i.e. when the start timing signal for capturing the contrast images is not inputted by the timing-inputting unit 30, performing the fluoroscope, and displaying the fluoroscopic images on the monitor 40.

As described above, according to the flow chart shown in FIG. 5, the first contrast images including the arterial phase are captured in Step S5a. Subsequently, the process returns from Step S6a to Step S11b, and the second contrast images including the venous phase are captured in Step S5b.

Then, the 2D-image data of the difference images is created by the image processing unit 41 from the 2D-image data of the mask images and the contrast images. Subsequently, the 3D-image data is created by reconstructing the 2D-image data by the 3D-image reconstructing unit 42. The resultant 3D-image data is retained and displayed in the 3D-workstation 43.

In Step S11, fluoroscopic images are displayed on the monitor 40. The fluoroscopic images may be not only simple fluoroscopic images but also subtractive fluoroscopic images. The subtractive fluoroscopic images are 2D images created by subtraction between the mask images captured in Step S2 and the fluoroscopic images. The subtractive fluoroscopic images displayed on the monitor 40 are clearer compared with the fluoroscopic images, and thus are able to be easily observed by doctors or the like.

According to the X-ray diagnostic imaging system 10 and the modification example of the X-ray diagnostic imaging method of the present invention, the contrast images including the arterial layer and the venous layer can be captured at one time. Thus, invasiveness on patients can be regulated, and also, 3D-DSA can be efficiently performed.

What is claimed is:

1. An X-ray diagnostic imaging method for radiographing a predetermined area of a subject with a rotational motion of a single C-arm so as to acquire image data of a contrast image including a figure of a contrast medium flowing in an affected part, and for displaying and retaining the image data of the contrast image, comprising:

acquiring a mask image of the predetermined area;

injecting a contrast medium into the affected part after acquiring the mask image;

starting a first radiograph of the predetermined area for a first contrast image when a time reaches an arterial phase after the injecting of the contrast medium into the affected part while rotating the C-arm in a first rotational direction; and starting a second radiograph of the predetermined area for a second contrast image after waiting for a time for the contrast medium to reach a venous phase after the arterial phase, while rotating the C-arm in a second rotational direction opposite to the first rotational direction.

2. The X-ray diagnostic imaging method according to claim 1, wherein reconstructing is done in the first contrast image and the second contrast image based on at least one image data, and a 3D-image data is acquired.

3. The X-ray diagnostic imaging method according to claim 2, wherein at least one image data of the mask image, the first contrast image, and the second contrast image is reconstructed.

4. The X-ray diagnostic imaging method according to claim 2, wherein at least one image data of a difference image between the mask image and the first contrast image, and a difference image between the mask image and the second contrast image is reconstructed.

5. The X-ray diagnostic imaging method according to claim 2, wherein the 3D-image data is displayed on a screen in the form of a 3D-image.

6. The X-ray diagnostic imaging method according to claim 5, wherein a 3D-image data of the mask image, the first contrast image, the second contrast image, a difference image between the mask image and the first contrast image, and a difference image between the mask image and the second contrast image are separately displayed on a screen in the form of a 3D-image.

7. The X-ray diagnostic imaging method according to claim 5, wherein at least two 3D-image data of the mask image, the first contrast image, the second contrast image, a difference image between the mask image and the first contrast image, and a difference image between the mask image and the second contrast image are created such that an image data fused at least two of 3D-image data of the mask image, the first contrast image, the second contrast image, the difference image between the mask image and the first contrast image, the difference image between the mask and the second contrast image are displayed on a screen in the form of a 3D-image.

8. The X-ray diagnostic imaging method according to claim 1, wherein the timing of the acquired start of the first contrast image and of the second contrast image are retained in advance such that when the timings come, the image data of the first contrast image and the second contrast image is acquired.

9. An X-ray diagnostic imaging system for radiographing a predetermined area of a subject with a rotational motion of a single C-arm so as to acquire image data of a contrast image including a figure of a contrast medium flowing in an affected part, and for displaying and retaining the image data of the contrast image, comprising:

a mask image performing unit configured to acquire a mask image of the predetermined area;

a first radiograph performing unit configured to start a first radiograph of the predetermined area for a first contrast image when a time reaches an arterial phase, after acquiring the mask image and after injection of the contrast medium into the affected part while rotating the C-arm in a first rotational direction; and a second radiograph performing unit configured to start a second radiograph of the predetermined area for a second contrast image after waiting for a time for the contrast medium to reach a venous phase after the arterial phase, while rotating the C-arm in a second rotational direction opposite to the first rotational direction.

10. The X-ray diagnostic imaging system according to claim 9, further comprising a 3D-image reconstructing unit for reconstructing the first contrast image and the second contrast image based on at least one image data, and for acquiring a 3D-image data.

11. The X-ray diagnostic imaging system according to claim 10, wherein the 3D-image reconstructing unit reconstructs at least one image data of the mask image, the first contrast image, and the second contrast image.

12. The X-ray diagnostic imaging system according to claim 10, further comprising an image processing unit for the performing subtraction so as to obtain a difference image between the mask image and the first contrast image, and a difference image between the mask image and the second contrast image such that the 3D-image reconstructing unit reconstructs at least one image data of the difference image between the mask image and the first contrast image, and the difference image between the mask image and the second contrast image.

13. The X-ray diagnostic imaging system according to claim 10, further comprising a displaying unit for displaying the 3D-image data on a screen in the form of a 3D-image.

14. The X-ray diagnostic imaging system according to claim 13, wherein the displaying unit separately displays the 3D-image data of the mask image, the first contrast image, the second contrast image, a difference image between the mask image and the first contrast image, and a difference image between the mask image and the second contrast image on a screen in the form of a 3D-image.

15. The X-ray diagnostic imaging system according to claim 13, wherein the displaying unit displays an image data fused at least two 3D-image data of the mask image, the first contrast image, the second contrast image, a difference image between the mask image and the first contrast image, and a difference image between the mask image and the second contrast image.

16. The X-ray diagnostic imaging system according to claim 9, further comprising a displaying unit for displaying a fluoroscopic image before acquiring the image data of the first contrast image and the second contrast image.

17. The X-ray diagnostic imaging system according to claim 9, further comprising a timing-retaining unit for retaining start timings of capturing contrast image as a preset value.

* * * * *